US011717582B2

(12) United States Patent
Imai

(10) Patent No.: US 11,717,582 B2
(45) Date of Patent: Aug. 8, 2023

(54) DISPENSER OF LIQUID PRODUCTS FOR SANITATION

(71) Applicant: Luiz Fernando Karasawa Imai, São Paulo (BR)

(72) Inventor: Luiz Fernando Karasawa Imai, São Paulo (BR)

(*) Notice: Subject to any disclaimer, the term of this patent is extended or adjusted under 35 U.S.C. 154(b) by 0 days.

(21) Appl. No.: 17/364,066

(22) Filed: Jun. 30, 2021

(65) Prior Publication Data

US 2022/0001046 A1 Jan. 6, 2022

(30) Foreign Application Priority Data

Jul. 1, 2020 (BR) ...................... 10 2020 013538 4

(51) Int. Cl.
| | | |
|---|---|---|
| *A61L 2/00* | (2006.01) | |
| *A47K 5/12* | (2006.01) | |
| *A61L 2/24* | (2006.01) | |
| *B05B 9/04* | (2006.01) | |

(52) U.S. Cl.
CPC .......... *A61L 2/0088* (2013.01); *A47K 5/1211* (2013.01); *A47K 5/1217* (2013.01); *A61L 2/24* (2013.01); *B05B 9/0403* (2013.01); *A61L 2202/14* (2013.01); *A61L 2202/15* (2013.01)

(58) Field of Classification Search
CPC ...... A61L 2/0088; A61L 2/24; A61L 2202/14; A61L 2202/15; A47K 5/1211; A47K 5/1217; B05B 9/0403; B05B 9/0423; B05B 12/122; B05B 13/02

See application file for complete search history.

(56) References Cited

U.S. PATENT DOCUMENTS

| | | | | |
|---|---|---|---|---|
| 2011/0174348 A1* | 7/2011 | Helenius | .............. | A47K 5/1217 134/56 R |
| 2019/0147731 A1* | 5/2019 | Herdt | ..................... | G08B 25/10 340/573.1 |

FOREIGN PATENT DOCUMENTS

| | | | | |
|---|---|---|---|---|
| BR | 20 2017 006301 7 | 3/2017 | | |
| BR | 20 2018 007939 0 | 4/2018 | | |
| BR | 11 2018 076230 0 | 12/2018 | | |
| DE | 202020000617 U1 * | 4/2020 | | |
| DE | 202020105682 U1 * | 11/2020 | | |
| DE | 102020003534 A1 * | 12/2021 | | |
| WO | WO-2004054460 A2 * | 7/2004 | ............. | A61B 90/80 |
| WO | WO-2021214322 A1 * | 10/2021 | ........... | A47K 5/1217 |
| WO | WO-2021228745 A1 * | 11/2021 | | |

* cited by examiner

*Primary Examiner* — Vishal Pancholi
(74) *Attorney, Agent, or Firm* — B. Aaron Schulman, Esq.; Stites & Harbison, PLLC

(57) ABSTRACT

A dispenser of liquid products for sanitization, such as bactericides, germicides, disinfectants, alcohol gel, moisturizers, among others, featuring innovative construction characteristics which distribute the product onto the user's hands or onto surfaces of various objects, via spraying in micro droplets, enabling a uniform distribution, suitable to be installed in public environments such as restrooms, restaurants, malls, offices and commercial facilities.

2 Claims, 5 Drawing Sheets

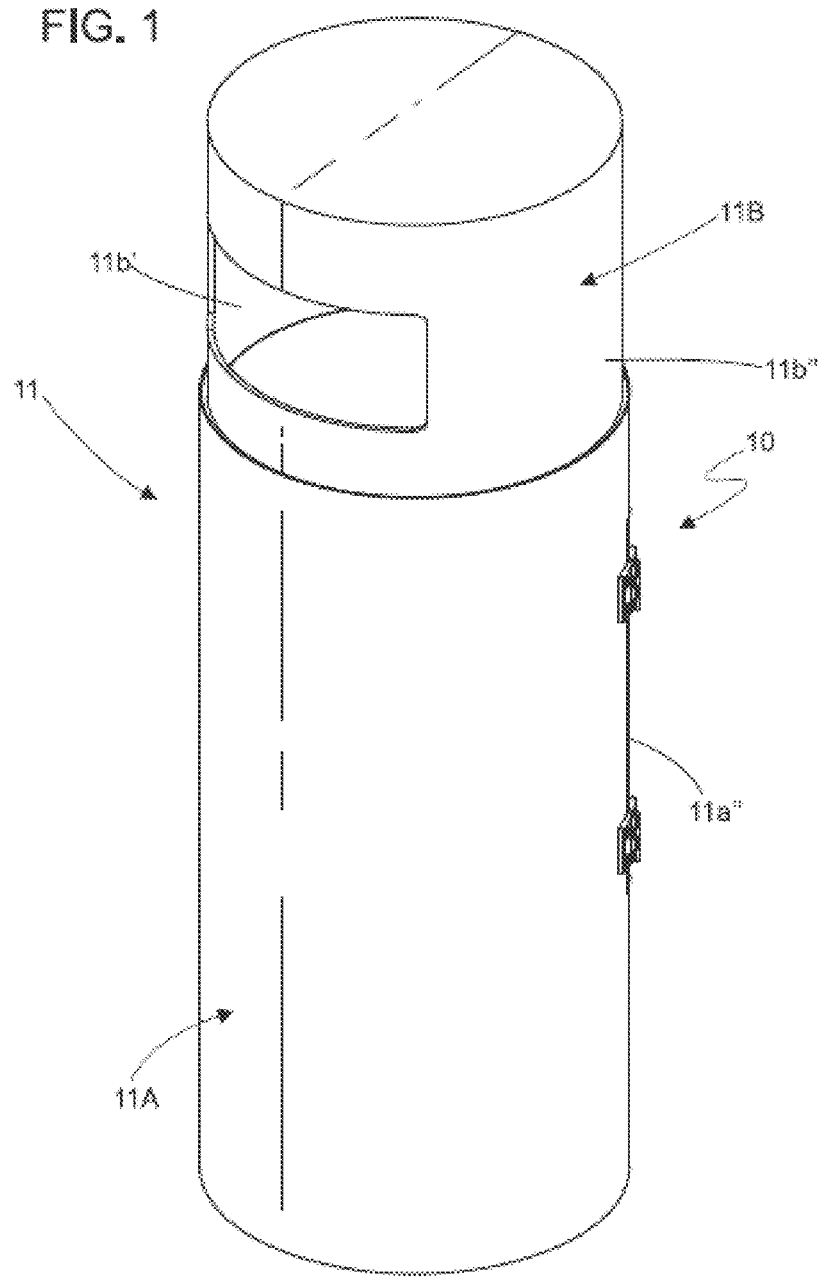

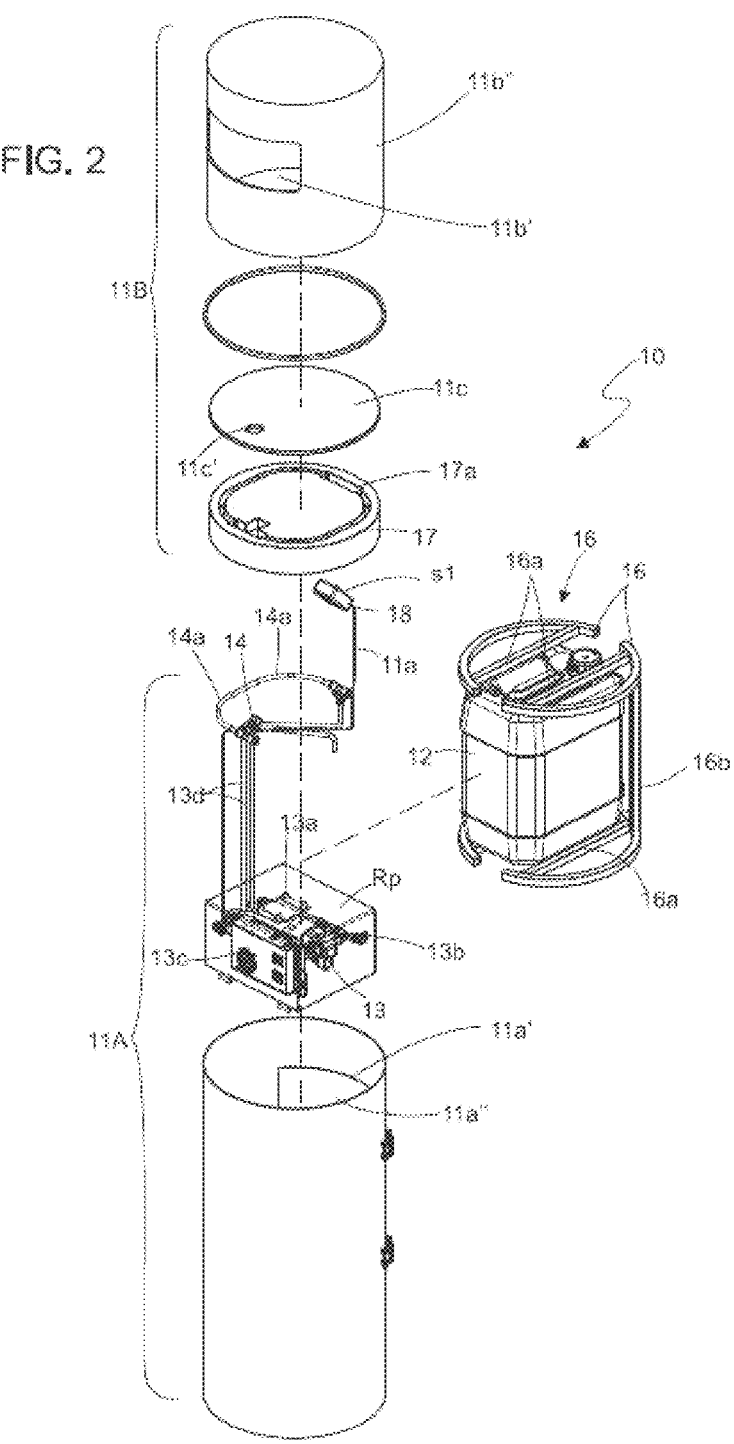

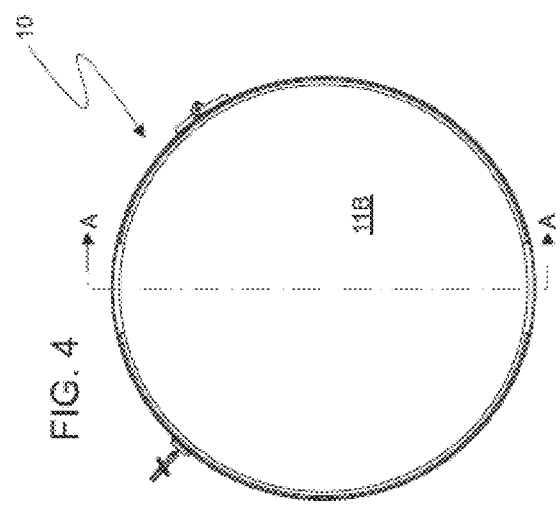
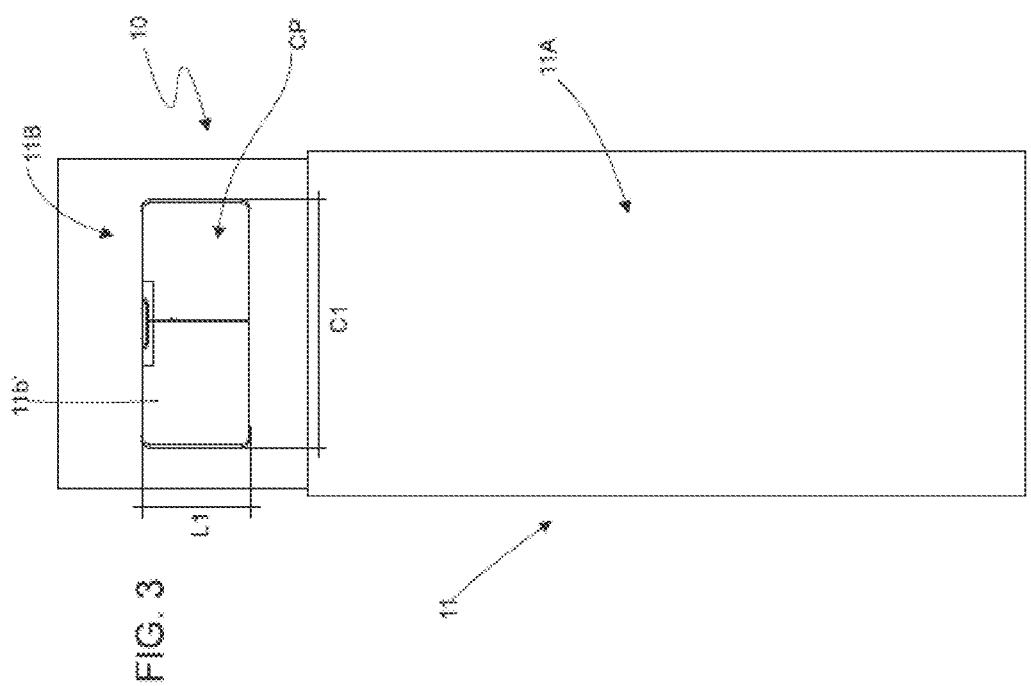

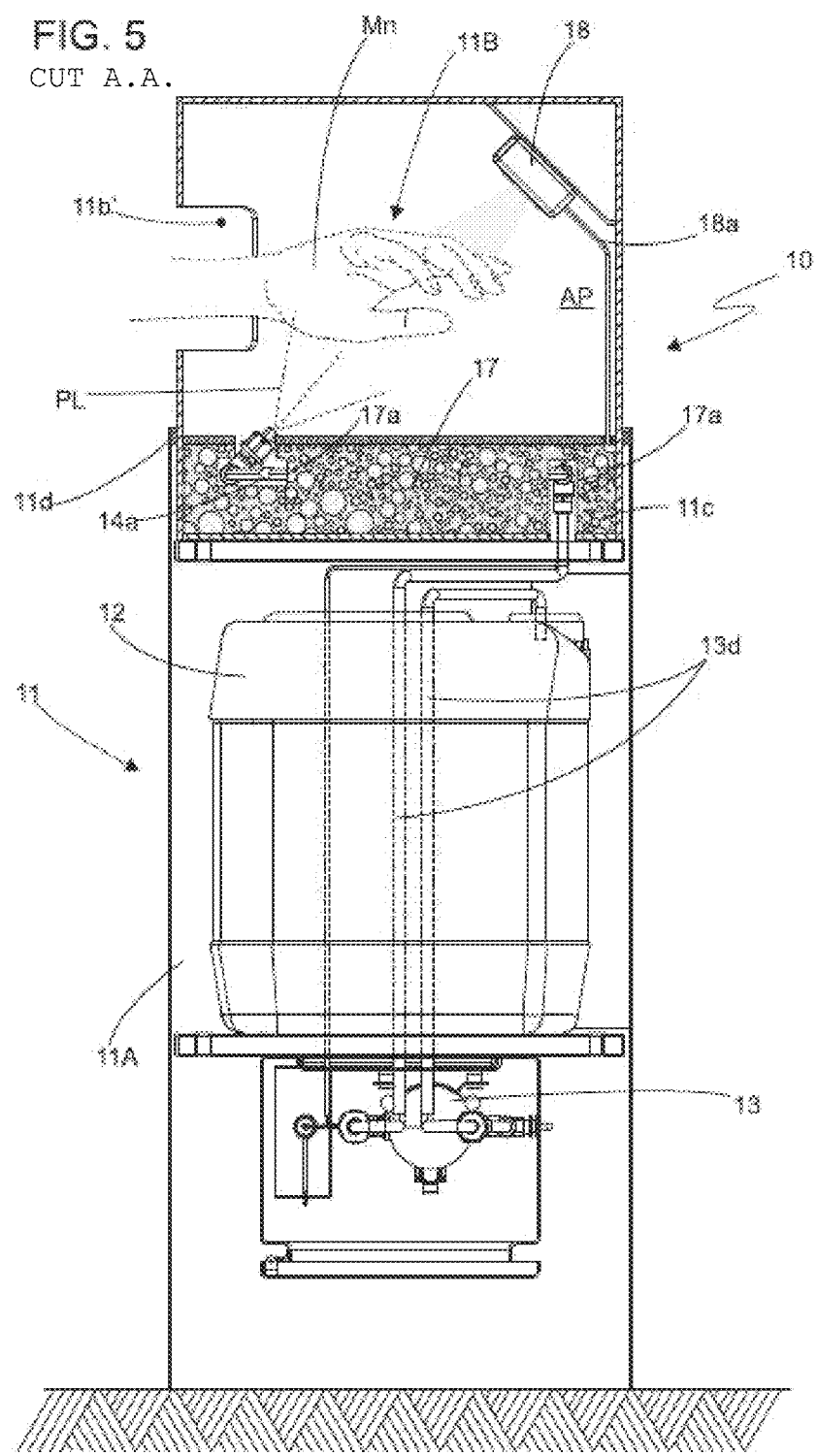

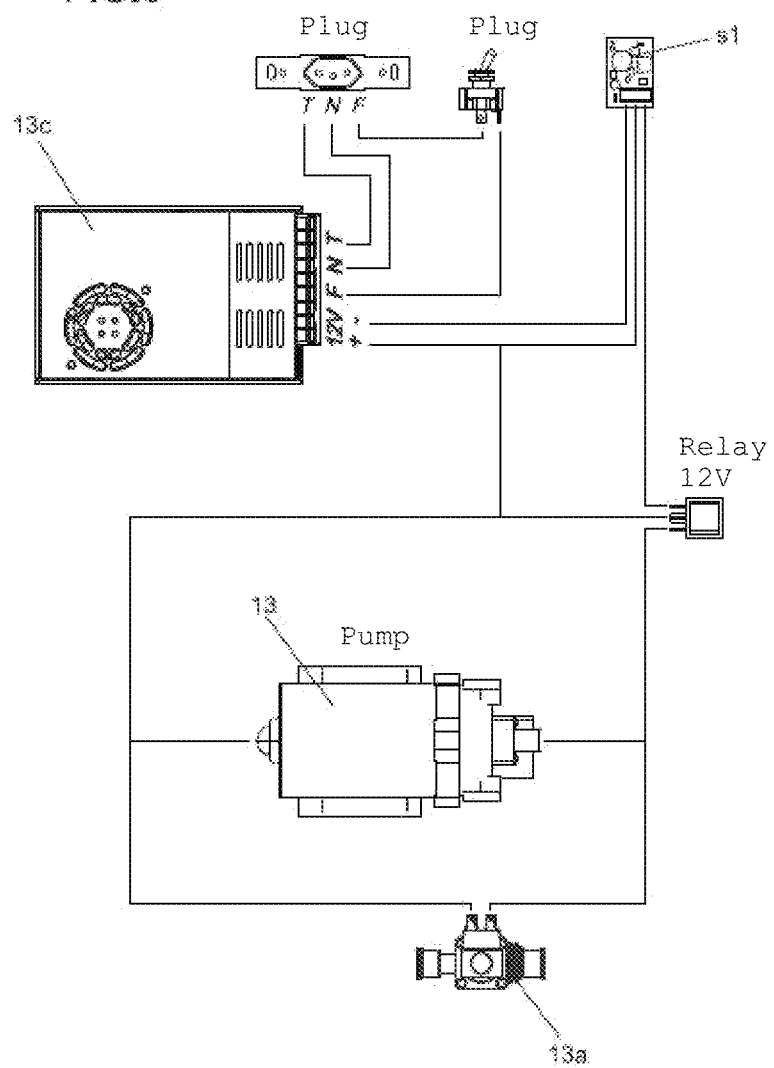

DISPENSER OF LIQUID PRODUCTS FOR SANITATION

TECHNICAL FIELD OF THE INVENTION

This invention patent refers to a dispenser of liquid products for sanitization such as bactericides, germicides, disinfectants, alcohol gel, moisturizers, among others, in which, notably, said dispenser features innovative construction characteristics that enable uniform distribution of the product on the user's hands or onto surfaces of various small objects; for this purpose, the dispenser is designed with a vertical structure or a spraying chamber, which includes a reservoir with minimum capacity of 2.5 liters and a pressure pump above 7 Bar, both provided in the lower section of said structure and associated to a spraying nozzle located on the upper section of said structure, in line with an access inlet. Therefore, when the user places his/her hands through the access inlet, the liquid or gel product is sprayed in micro droplets, which adhere and cover the entirety of the desired surface, decreasing consumption of the dispensed product and increasing distribution efficiency.

BACKGROUND OF THE INVENTION

As is widely known, the use of alcohol gel or other bactericide products, germicides and disinfectants have become increasingly frequent, necessary, and mandatory. Models for dispensers of liquid, gel, or foam products, such as soap, alcohol gel, moisturizers, among others, are usually used in public locations such as restrooms, restaurants, malls, offices, and various commercial facilities, in order to facilitate product access, as well as its replenishment.

Currently, countless dispenser models for said liquid, gel or foam products are known, in which the manual model is basically comprised of a bottle-type reservoir with a dosing valve mounted onto the nozzle, which, when pressed down, dispenses the liquid/gel/foam product onto the hands of the user.

The drawback of this manual dispenser model lies in the fact that the product is dispensed according to the force applied by the user onto the dosing valve associated to the course of the activation trigger, thus allowing higher or lower product amounts to be dispensed.

Another drawback lies in the fact that constant valve handling for dispensing liquid/gel/foam product in a public location is not recommended due to the accumulation of impurities and dissemination of bacteria, germs, and viruses, particularly, during a pandemic.

Another dispenser model, which is widely known in the market, is automatic and also comprises a reservoir with a pumping mechanism for the liquid/gel/foam product, reserved and assembled into a batcher, in turn, activated by a detection sensor or infrared device that dispenses the liquid/gel/foam when the user's hands approach.

The drawback of the automatic model, similarly to the manual mode, lies in the fact that the product is dispensed as a jet and on a single spot, a feature that hinders uniform spreading, thus depending on rubbing of the user's hands.

In a search carried out on specialized databases, documents referring to spraying were found for dispensers for liquid or gel products, such as bactericides, germicides, disinfectants, alcohol gel, moisturizers, among others, such as document No. BR 20.2017.006301-7 which refers to an automatic dispenser for commercialization of cleaning products placed inside a self-servicing machine for commercialization and provision of liquid cleaning products, which comprises a dispenser window; LCD display; selection button; confirm button; dispenser nozzle; bottle; charge cell; credit card machine; money bill reader; coin reader; hose; motor pump; container; motor pump valve; electronic board; dosing valve or flow sensor and dispenser.

Document No. BR 20.2018.007939-0 refers to a dispenser to store liquid soap or alcohol gel which may be attached directly to the container used for water transportation, on the truck's lower section or chassis; this product provides greater convenience to truck drivers which need to sanitize their hands several times during their trips.

Document No. BR11.2018.076230-0 discloses a liquid dispenser for particular discharging of pharmaceutical liquids, including a discharge head and a cover, with a vent opening included on said cover's structure. Provision of an injected extraction segment is proposed, which, on a supply state, covers the vent opening and is tightly held together with the cover structure. This extraction segment is joined with an originality segment, which, in the supply state of the dispenser, prevents removal of the cover structure, part of a separable segment of the cover structure from the cover. In another configuration, the vent opening is provided with an air current filtering membrane, with the cover structure including two partial structures that jointly assemble a housing chamber for the filtering membrane.

The aforementioned documents, although belonging to the same field of application, are distinguished from this invention, as may be seen in the following sections, thus ensuring that it fully addresses the legal patentability requirements.

SUMMARY OF THE INVENTION

It is an objective of the invention to provide a dispenser of liquid products for sanitization, such as bactericides, germicides, disinfectants, alcohol gel, moisturizers, among others, said dispenser featuring innovative construction characteristics which distribute the product onto the user's hands or onto surfaces of various objects, via spraying in micro droplets, in other words, a uniform distribution.

For this reason, the product spraying dispenser comprises a small-sized structure or spraying chamber that houses a reservoir with a minimum capacity of 2.5 liters, a pressure pump above 7 Bar and, at least, one dispensing nozzle. This set is able to produce, when activated, the spraying of the sanitization product in micro droplets over the entire desired surface, rapidly covering it, while reducing excessive consumption of the dispensed product, thus increasing distribution efficiency.

It is an objective of the invention to provide a dispenser of liquid products for sanitization, comprising a protection casing with an opening for access to a spraying chamber, so that the user's hands or any objects to be disinfected may be inserted, where a sensor installed in the chamber detects the presence of a body, and one or more of the spraying nozzles dispense the product, in order to ensure the best coverage possible.

Another objective of this invention is to provide a dispenser of liquid products for sanitization, wherein the spraying chamber that comprises the protection casing enables better spreading and coverage area of the sprayed product, thus preventing that the droplets are lost due to evaporation or wind action.

It is also an objective of this invention to provide a dispenser of liquid products for sanitization, with a detection sensor that activates the pump for spraying the product held in the reservoir for a time period programmed by a timer.

It is an objective of this invention to provide a dispenser of liquid products for sanitization, including a pump with pressure above 7 BAR that causes the liquid to be sprayed with droplets smaller than 150 Microns, adhering and covering the surface of the hands or small objects inserted in said chamber, thus causing the amount of product dispensed to be lower than the standard manual spreading through standard valves, but with equal or higher efficiency.

Another objective of this invention is to provide a dispenser of liquid products for sanitization which allows application of 5 ml to 500 ml per activation, in a safe and accurate manner, according to the predefined timer setting which may be, for example, around 10 to 15 seconds.

It is also an objective of this invention to provide a dispenser of liquid products for sanitization which may be installed on all kinds of environments, such as places with large circulation of people, malls, companies, among others.

BRIEF DESCRIPTION OF THE DRAWINGS

FIG. 1 shows an assembled perspective view of the dispenser of liquid products for sanitization;

FIG. 2 shows an exploded perspective view of the elements that comprise the dispenser of liquid products for sanitization;

FIG. 3 shows a front view;

FIG. 4 shows an upper view;

FIG. 5 represents a A.A sectioned longitudinal view indicated in the previous figure, showing the accessibility of the spraying chamber; and FIG. 6 shows the electric scheme of the dispenser.

DETAILED DESCRIPTION OF THE INVENTION

Referring to the drawings shown, this invention patent refers to a "DISPENSER OF LIQUID PRODUCTS FOR SANITIZATION", more precisely, a dispenser (10) for installation in public environments such as restrooms, restaurants, malls, offices, and commercial facilities, which was conceived to dispense liquid or gel products such as bactericides, germicides, disinfectants, alcohol gel, moisturizers, among others. Said dispenser (10) comprises a protection casing (11) which may house a reservoir gallon (12), and a pressurization pump (13).

According to this invention, said protection casing (11) is formed by two complementary parts of corresponding dimensions, with an enclosure (11A) housing the reservoir gallon (12) for liquid/gel products (PL), with a minimum capacity of 2.5 liters, and electronic components placed within an enclosure (Rp) such as the pressurization pump (13) associated to an anti-dripping valve (13a) and a solenoid valve (13b) supplied by a 12 V source (13c), in addition to piping (13d), as well as receiving support (16) by the reservoir gallon (12), whereas the upper dome (11B) receives one or more spraying nozzles (14) connected through pipelines (14a) and (13d) next to the pump (13) and at least one sensor (s1) that detects the access of hands (Mn) through the opening (11b') on the upper dome (11B).

Said upper dome (11B) is formed by a tubular cylinder body (11b") that houses a discoid base (11c) formed by a synthetic turf board or any other suitable material and provided with cut-out (11c'), said board (11c) may receive a rim on its edge (11d). Said dome (11B) features a front opening (11b') with a width (L1) and length (C1) capable of comprising the spraying chamber (CP) that receives the hands (Mn) of the user or other small objects to be disinfected (not shown).

Said spraying chamber (CP) may receive one or more spraying nozzles (14) interconnected into pipelines (14a) settled into a channel (17a) carried out on a secondary base (17) juxtaposed to the discoid base (11c) and manufactured in resilient material such as, for example, foam. Said pipelines (14a) are connected through flexible pipes (13d) in the pressurization pump (13) with a pressure above 7 BAR so that the liquid/gel is sprayed in drops smaller than 150 Microns, adhering and covering the surface of the hands (Mn) and objects inserted in the spraying chamber (AP).

Said spraying chamber (AP) comprises a sensor (s1) mounted to a protective box (18) which, is turn, is connected to an orthogonal rod (18a) and which detects the access of hands (Mn) through the opening (11b') of the dispenser (10) and activates the pump (13) to spray the product for a predefined timer setting, for example, around 10 to 15 seconds, allowing dispensing of 5 ml to 500 ml per activation, as well as ensuring that the sprayed product covers the entirety of the desired surface for disinfection.

The reservoir gallon (12) is installed between semi-annular supports (16) including crossbars (16a) and interconnected via an orthogonal profile (16b), provided the supports (16) are aligned with the enclosure openings (11A).

Said enclosure (11A) is provided with an opening (11a') for the assembly of a swivel door (11a") for when the reservoir gallon (12) needs to be replaced.

This invention certainly allows for modifications when deployed in a functioning state, regarding certain construction and form details, with no deviation from the main principles that are clearly stated in the set of claims, and with full understanding that the terminology used is not intended to be limiting.

The invention claimed is:

1. A dispenser of liquid or gel products for sanitization, comprising:
    a protection casing capable of housing a reservoir gallon of at least 2.5 liters of liquid or gel,
    a pressurization pump,
    a hand motion sensor,
    an upper dome; and
    one or more spraying nozzles connected by one or more pipelines to the pressurization pump and to the reservoir gallon;
    wherein the protection casing is formed by two complementary sections of corresponding dimensions comprising a first enclosure containing the reservoir gallon, said first enclosure arranged above a second enclosure containing the pressurization pump, said pressurization pump also containing an anti-dripping valve and said one or more pipelines;
    wherein the reservoir gallon is housed in semi-annular supports having crossbars interconnected by an orthogonal profile,
    wherein the semi-annular supports are aligned with the first enclosure;
    wherein the upper dome is arranged above the first enclosure and is formed by a tubular cylinder body having an opening forming a spraying chamber and containing a discoid base formed by a foam plate having a cutout, said discoid base having a rim on an edge; and
    wherein the one or more pipelines access the one or more spraying nozzles and are seated in a channel made on a secondary base juxtaposed to the discoid base.

2. The dispenser according to claim 1, wherein the pressurization pump has a pressure greater than 7 BAR so that the liquid or gel is sprayed in drops smaller than 150 microns.

\* \* \* \* \*